(12) United States Patent
Wei et al.

(10) Patent No.: US 9,829,439 B2
(45) Date of Patent: Nov. 28, 2017

(54) TEST STRIP DEVICE

(71) Applicants: LITE-ON ELECTRONICS (GUANGZHOU) LIMITED, Guangzhou (CN); LITE-ON TECHNOLOGY CORPORATION, Taipei (TW)

(72) Inventors: Chia-Chun Wei, Taichung (TW); Szu-Hsien Ho, Hsinchu (TW); Hung-Wei Chen, Taichung (TW)

(73) Assignees: LITE-ON ELECTRONICS (GUANGZHOU) LIMITED, Guangzhou (CN); LITE-ON TECHNOLOGY CORPORATION, Taipei (TW)

( * ) Notice: Subject to any disclaimer, the term of this patent is extended or adjusted under 35 U.S.C. 154(b) by 58 days.

(21) Appl. No.: 15/047,720

(22) Filed: Feb. 19, 2016

(65) Prior Publication Data

US 2017/0160204 A1    Jun. 8, 2017

(30) Foreign Application Priority Data

Dec. 7, 2015  (CN) .................... 2015 2 1004963 U

(51) Int. Cl.
    *G01N 21/77*   (2006.01)
    *B01L 3/00*    (2006.01)
    *G01N 21/75*   (2006.01)

(52) U.S. Cl.
CPC ............. *G01N 21/77* (2013.01); *B01L 3/502* (2013.01); *B01L 2200/06* (2013.01); *B01L 2300/0803* (2013.01); *B01L 2300/0848* (2013.01); *B01L 2300/0864* (2013.01); *B01L 2300/12* (2013.01); *B01L 2400/08* (2013.01); *G01N 2021/752* (2013.01); *G01N 2021/754* (2013.01); *G01N 2021/7759* (2013.01)

(58) Field of Classification Search
CPC ............. G01N 21/77; G01N 2021/752; G01N 2021/754; G01N 2021/7759; B01L 3/502; B01L 2300/12; B01L 2300/0803; B01L 2300/0864; B01L 2400/08; B01L 2200/06; B01L 2300/0848
See application file for complete search history.

(56) References Cited

U.S. PATENT DOCUMENTS

2007/0166200 A1*   7/2007   Zhou ..................... B01L 3/5025
                                                             422/400

* cited by examiner

*Primary Examiner* — Lore Jarrett
(74) *Attorney, Agent, or Firm* — Li & Cai Intellectual Property (USA) Office

(57) ABSTRACT

Disclosed is a test strip device, comprising a strip body and a blocking element. The strip body has a first face and a second face. The strip body has an injection opening, a flow channel and a reaction receptacle. The injection opening reaches the first face, the flow channel is in fluid communication between the injection opening and the reaction receptacle, and the flow channel is in fluid communication with the injection opening through a flow channel opening. The blocking element is vertically movably disposed in the injection opening, and the blocking element selectively closes the flow channel opening. Therefore, the back flow of a sample can be prevented, so as to ensure chemical reaction of the sample and a reagent and thus improve accuracy of the test results.

19 Claims, 14 Drawing Sheets

TEST STRIP DEVICE

TECHNICAL FIELD

The present disclosure relates to a test strip device, and in particular to a strip device for testing and analyzing a sample such as blood, urine or saliva.

BACKGROUND ART

A conventional blood test strip is used for testing and analyzing blood. During the use of the blood test strip, the reaction of blood and reagents must be controlled within a reaction region, and if the back flow of the blood and reagents occurs during the reaction, precision of measured values may be affected, thereby affecting accuracy of the test results. Also, the same problems exist for test strips of solution samples such as urine or saliva.

In view of the above disadvantages, after extensive research in conjunction with theoretical knowledge, the inventor provides the present disclosure that is reasonably designed and effectively improves upon the above disadvantages.

SUMMARY OF THE INVENTION

The technical problem to be solved by the present disclosure is to provide a test strip device capable of preventing the back flow of a sample, so as to ensure chemical reaction of the sample and reagents and thus improve accuracy of the test results.

In order to solve the technical problem above, the present disclosure provides a test strip device, including: a strip body having a first face and a second face at opposite sides thereof and having an injection opening, a flow channel and a reaction receptacle, wherein the injection opening reaches the first face, the flow channel is in fluid communication between the injection opening and the reaction receptacle, and the flow channel is in fluid communication with the injection opening through a flow channel opening; and a blocking element vertically movably disposed in the injection opening and selectively closing the flow channel opening.

In order to solve the technical problem above, the present disclosure also provides a test strip device, including: a strip body having a first face and a second face at opposite sides thereof and having an injection opening, a flow channel and a reaction receptacle, wherein the injection opening reaches the first face, the flow channel is in fluid communication between the injection opening and the reaction receptacle, and the flow channel is in fluid communication with the injection opening through a flow channel opening; a blocking element vertically movably disposed in the injection opening and selectively closing the flow channel opening; and a tray having a protruding portion, wherein the strip body is placed on the tray, and the protruding portion presses against the blocking element, such that the blocking element is raised to close the flow channel opening.

The instant disclosure has at least the following advantages:

According to the present disclosure, a blocking element is disposed at the injection opening of the strip body, and the blocking element does not block the flow channel opening to affect injection of the sample. After the sample is injected, the reaction receptacle is filled with the sample by the capillary force of each flow channel Then, the blocking element may be pushed upward, and each flow channel opening is effectively blocked from the injection opening by the movement of the blocking element, so as to prevent possible diffusion of pollutants among the reaction receptacles and back flow.

Furthermore, the strip body has an air vent, and the air vent is located on the first face and in fluid communication with one end of the reaction receptacle distal from the flow channel Air within the reaction receptacle may be discharged through the air vent, such that the sample may enter into the reaction receptacle smoothly while there is no air lock, so as to avoid affecting the accuracy of the test results.

In order to further understand the features and technical content of the present disclosure, reference can be made to the detailed description and accompanying drawings of the present disclosure. However, the accompanying drawings are only provided for reference and illustration, and are not intended to limit the present disclosure.

DETAILED DESCRIPTION OF THE PREFERRED EMBODIMENTS

First Embodiment

Figure 1:
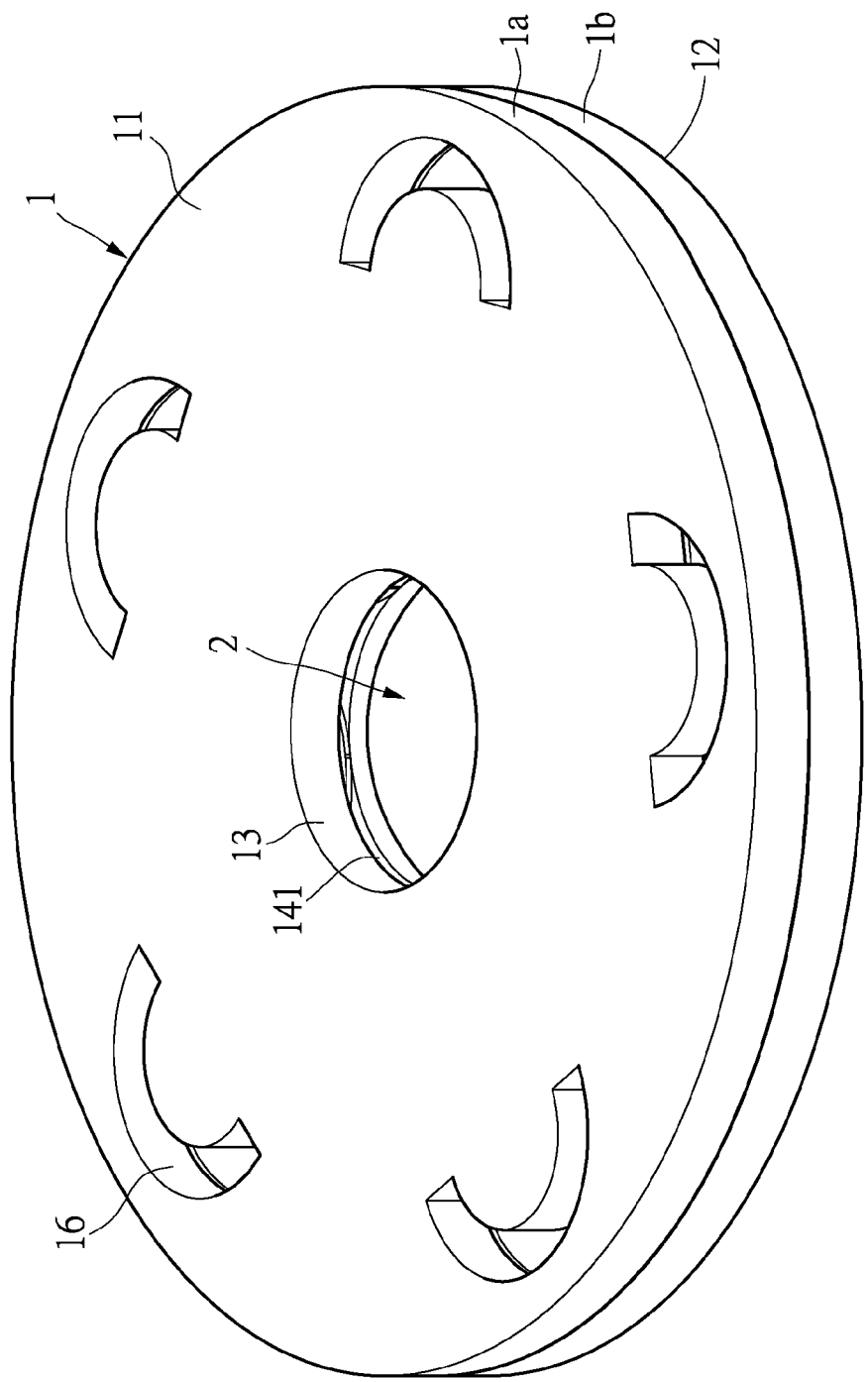
FIG. 1 is a perspective view of a first embodiment of a test strip device of the present disclosure.
Figure 2:
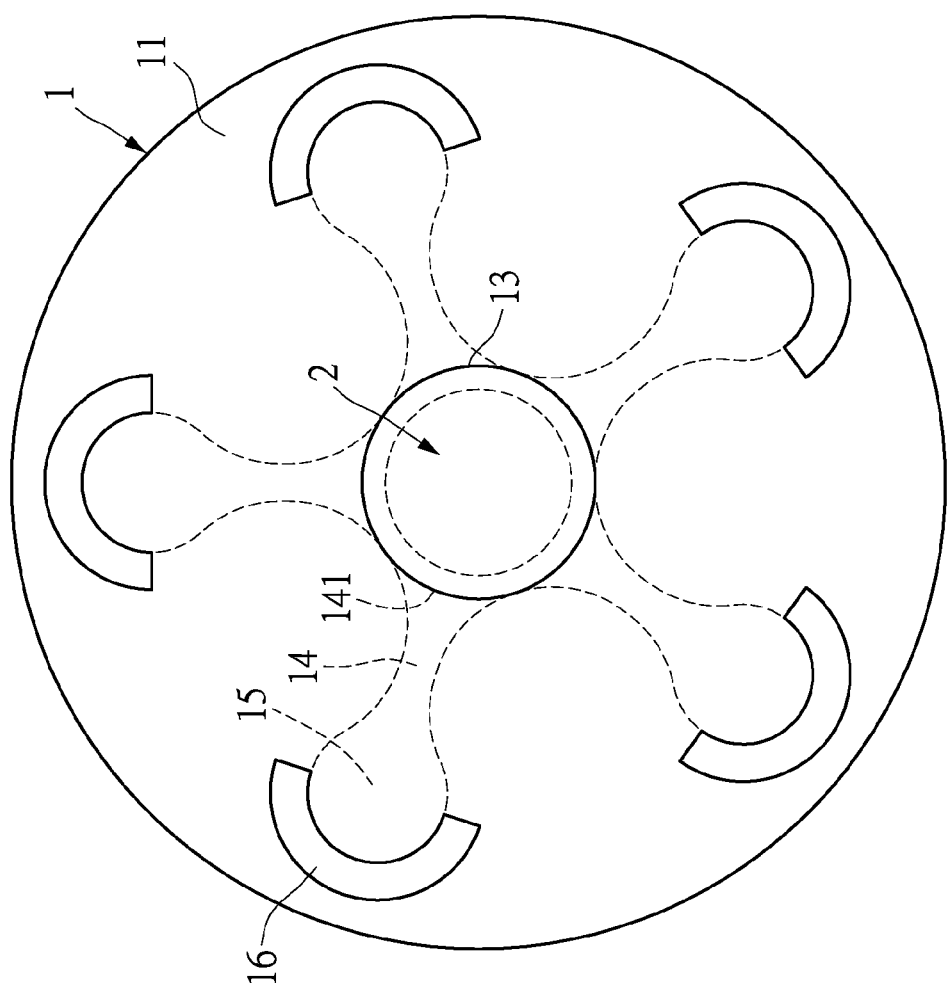
FIG. 2 is a top view of the first embodiment of the test strip device of the present disclosure.
Figure 3:
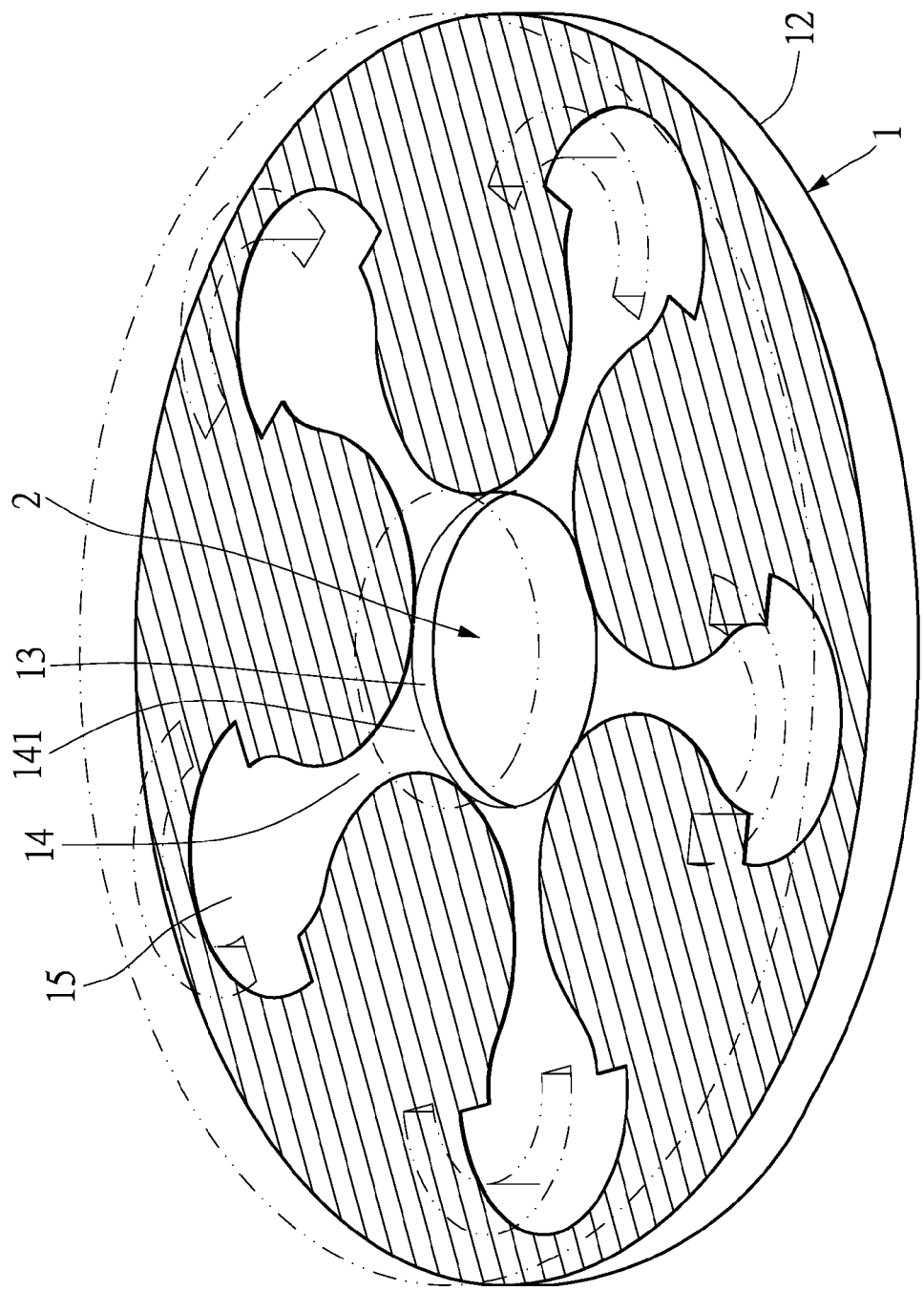
FIG. 3 is another perspective view of the first embodiment of the test strip device of the present disclosure.

Referring to FIG. 1 to FIG. 3, the present disclosure provides a test strip device, in particular a strip device for testing and analyzing a liquid sample such as blood, urine or saliva, and the test strip device includes a strip body 1 and a blocking element 2.

The strip body 1 is preferably made of a transparent material, in order to test and analyze the sample with an optical method. The strip body 1 is in the form of a sheet. The shape thereof is not limited, and in the present embodiment, the strip body 1 is in the form of a circular sheet. The strip body 1 may comprise an upper body 1a and a lower body 1b, and the upper body 1a and the lower body 1b are combined into one single body for ease of manufacture. However, the construction of the strip body 1 is not limited and may be a one-piece, two-piece, or multi-piece construction.

The strip body 1 has a first face 11 and a second face 12 at opposite sides thereof In the present embodiment, the first face 11 and the second face 12 are located on a top face and a bottom face of the strip body 1, respectively.

The strip body 1 has injection opening(s) 13, flow channel(s) 14 and reaction receptacle(s) 15. The number of injection openings 13 provided is most often one, while the number of flow channels 14 and reaction receptacles 15 may be one, two or several. However, the numbers thereof are not limited. In the present embodiment, the number of both the flow channels 14 and the reaction receptacles 15 is five, and naturally the number may also be three, four or six, and so on.

The position where the injection opening 13 is provided on the strip body 1 is not limited. In the present embodiment, the strip body 1 is in the form of a circular sheet, and the injection opening 13 is arranged at or near the center of the strip body 1. The injection opening 13 may be in the shape of a circular aperture, an oval aperture, a square aperture or in other shapes; the shape of the injection opening 13 is not limited. The injection opening 13 reaches the first face 11, such that a top end of the injection opening 13 is open, in order to allow injection of a sample (for example, blood) into the injection opening 13 from the top of the strip body 1.

Figure 4:
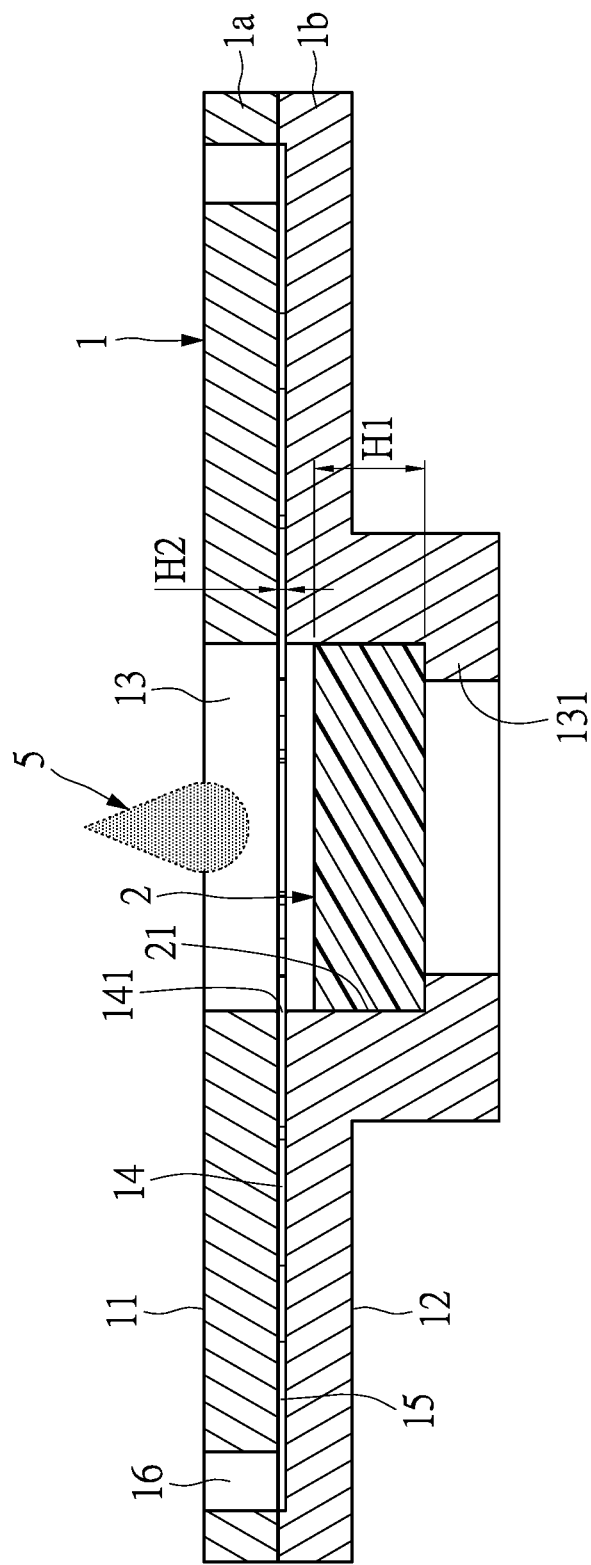
FIG. 4 is a cross-sectional view of the first embodiment of the test strip device of the present disclosure.

The injection opening 13 may further reach the second face 12 (as shown in FIG. 4), and an inner wall of the injection opening 13 may have a bearing portion 131 proximal to the second face 12. The bearing portion 131 may be formed by the horizontal extension of the inner wall of the injection opening 13, and the bearing portion 131 extends horizontally by some distance toward the center of the injection opening 13, such that the bearing portion 131 protrudes from the inner wall of the injection opening 13. The bearing portion 131 may be disposed at the inner wall of the injection opening 13 as a continuous or discrete ring. The blocking element 2 may be disposed on the bearing portion 131, and the bearing portion 131 may be used to stop and position the blocking element 2 to prevent the blocking element 2 from moving downward and exiting the injection opening 13.

The flow channel 14 is in fluid communication between the injection opening 13 and the reaction receptacle 15. The shape of the flow channel 14 is not limited and in the present embodiment, the flow channel 14 is gradually enlarged from the middle to both ends. Each flow channel 14 is in fluid communication with the injection opening 13 through a flow channel opening 141, such that one end of the flow channel 14 is in fluid communication with the injection opening 13. The other end of the flow channel 14 is in fluid communication with the reaction receptacle 15, such that the flow channel 14 is in fluid communication between the injection opening 13 and the reaction receptacle 15. A reagent (not shown) may be placed in the reaction receptacle 15, and the reagent may be appropriately dried to be adhered within the reaction receptacle 15. After a sample 5 is injected into the injection opening 13 (as shown in FIG. 4), the sample 5 may pass through each flow channel 14 and fill the reaction receptacle 15 by the capillary force of each flow channel 14, such that the sample 5 may react with the reagent in the reaction receptacle 15. If several reaction receptacles 15 are provided, different reagents may be placed in these reaction receptacles 15 to perform different tests and analysis, for example, tests and analysis for blood glucose, blood lipid or cholesterol.

In the present embodiment, there are several flow channels 14 and reaction receptacles 15. These flow channels 14 are in fluid communication between the injection opening 13 and these reaction receptacles 15, respectively. These flow channels 14 and these reaction receptacles 15 are disposed at a periphery of the injection opening 13 and in a radiating arrangement. However, the manner of arrangement is not limited. In addition, these flow channels 14 and these reaction receptacles 15 may be arranged with a uniform angular spacing between each other, but the arrangement is not limited to a uniform angular spacing.

The flow channel 14 and the reaction receptacle 15 may be located between and disposed spaced apart from the first face 11 and the second face 12, such that the flow channel 14 and the reaction receptacle 15 are located inside the strip body 1. The shape of the reaction receptacle 15 is not limited, and in the present embodiment, the reaction receptacle 15 is generally circular.

The strip body 1 of the present disclosure may further have an air vent 16 at one end of each reaction receptacle 15 distal from the flow channel 14. The air vent 16 may be arc-shaped or in other shapes, and is not limited thereto. The air vent 16 is arranged on the first face 11, and is in fluid communication with the reaction receptacle 15. Air within the reaction receptacle 15 may be discharged through the air vent 16, such that the sample 5 may enter into the reaction receptacle 15 smoothly while there is no air lock, so as to avoid affecting the accuracy of the test results.

The blocking element 2 may be made of silica gel or rubber, and may be a sheet in a circular, an oval, a square or other shapes. The shape of the blocking element 2 is not limited, and in the present embodiment, the blocking element 2 is a circular sheet corresponding to the injection opening 13. The blocking element 2 is vertically movably disposed in the injection opening 13; that is, the blocking element 2 may be pushed in the injection opening 13 to move vertically, such that the blocking element 2 may selectively close the flow channel opening 141.

In particular, an outer edge of the blocking element 2 is formed with a blocking face 21, and the height H1 of the blocking face 21 is greater than the height H2 of the flow channel opening 141 (as shown in FIG. 4), such that the blocking element 2 can selectively close the flow channel opening 141 with the blocking face 21. The blocking element 2 normally descends to the bottom of the injection opening 13 due to gravity, and the blocking element 2 may be disposed on the bearing portion 131, where the flow channel opening 141 is in an open state. Once the blocking element 2 is pushed upward to correspond to the flow channel opening 141, the flow channel opening 141 is closed by the blocking face 21 of the blocking element 2, such that the sample 5 cannot flow back to the injection opening 13.

Figure 5:
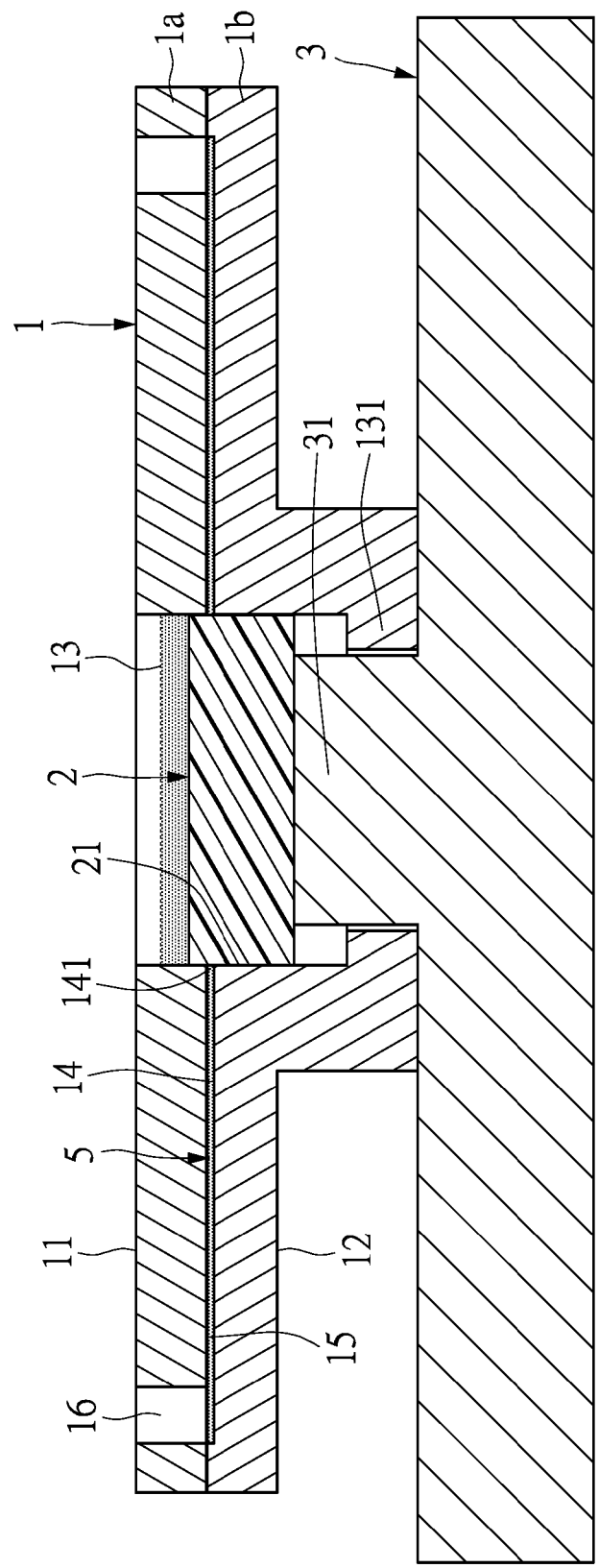
FIG. 5 is a cross-sectional view of the first embodiment of the test strip device of the present disclosure in a blocked state.

Referring to FIG. 5, the strip body 1 of the present disclosure may be disposed on a tray 3; that is, the strip body 1 may be placed on the tray 3 of the test and analysis device to perform analysis on the sample 5. The tray 3 has a protruding portion 31 protruding from a top face of the tray 3. The protruding portion 31 is a protruding structure having an outer diameter smaller than an inner diameter of the injection opening 13. In the present embodiment, the protruding portion 31 is fixedly disposed on the tray 3. When the strip body 1 is disposed on the tray 3, the protruding portion 31 may be inserted into the injection opening 13, and the protruding portion 31 may be used to press against the blocking element 2, such that the blocking element 2 is raised by a suitable height to close the flow channel opening 141. Namely, the protruding portion 31 may press against the blocking element 2 to move it upward to a position flush with the flow channel opening 141, such that the blocking face 21 of the blocking element 2 may close the flow channel opening 141 to obstruct the path of back flow of the sample 5.

According to the present disclosure, a blocking element 2 is disposed at the bottom of the injection opening 13 of the strip body 1, and the blocking element 2 does not block the flow channel opening 141 to affect injection of the sample 5 (for example, blood). After the sample 5 is injected, the reaction receptacle 15 is filled with the sample 5 by the capillary force of each flow channel 14. The strip body 1 is then placed on the tray 3 of the test and analysis device to perform analysis on the sample 5, and the blocking element 2 can be pushed upward by the protruding portion 31 on the tray 3 during the placement of the strip body 1. Each flow channel opening 141 is effectively blocked from the injection opening 13 by the movement of the blocking element 2, so as to prevent possible diffusion of pollutants among the reaction receptacles 15 and back flow.

In addition, after entering into the reaction receptacle 15 from the injection opening 13 through the flow channel 14, the sample 5 (for example, blood) chemically reacts with the reagent in the reaction receptacle 15. Since moisture is contained in the sample 5, vaporization of the moisture may occur when the sample is placed in the atmosphere. In view of this, according to the present disclosure, a blocking element 2 is plugged outside the flow channel opening 141 in the reaction process, whereby the back flow of the sample is effectively prevented, so as to ensure chemical reaction of the sample and the reagent and thus improve accuracy of the test results.

Second Embodiment

Figure 6:
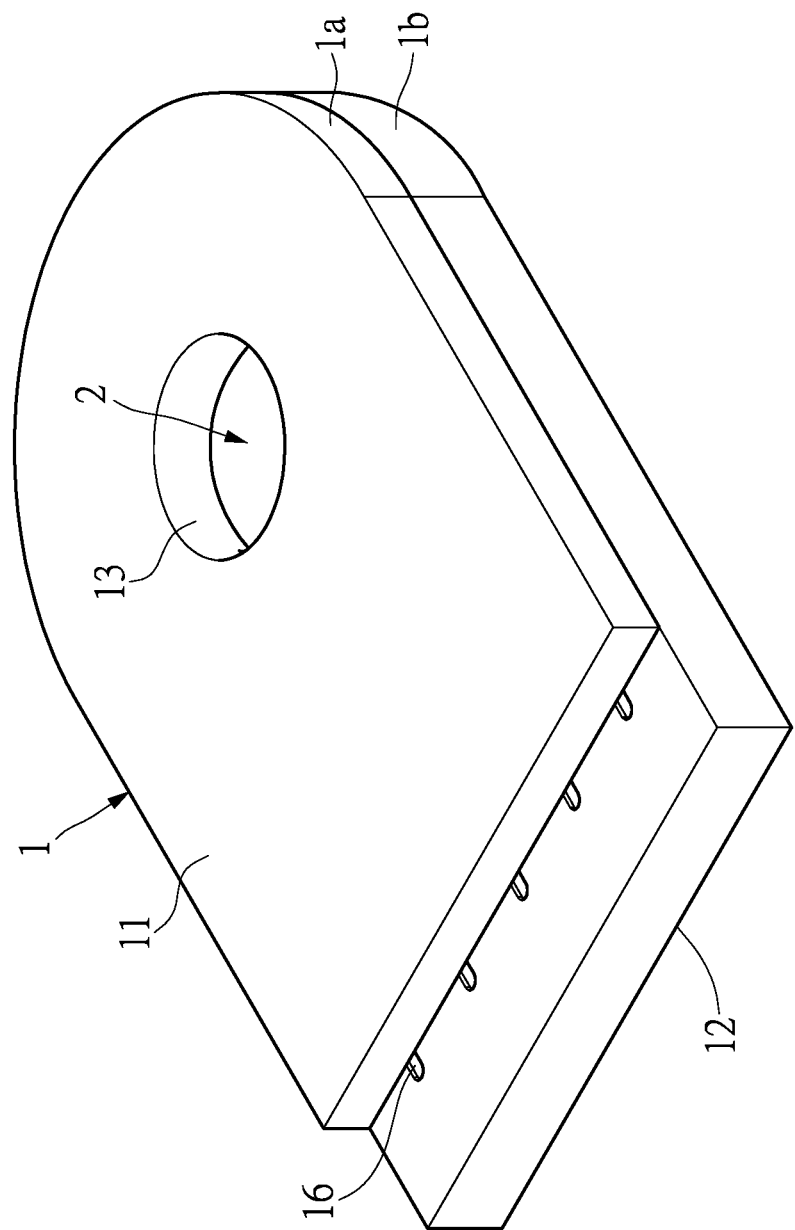
FIG. 6 is a perspective view of a second embodiment of the test strip device of the present disclosure.
Figure 7:
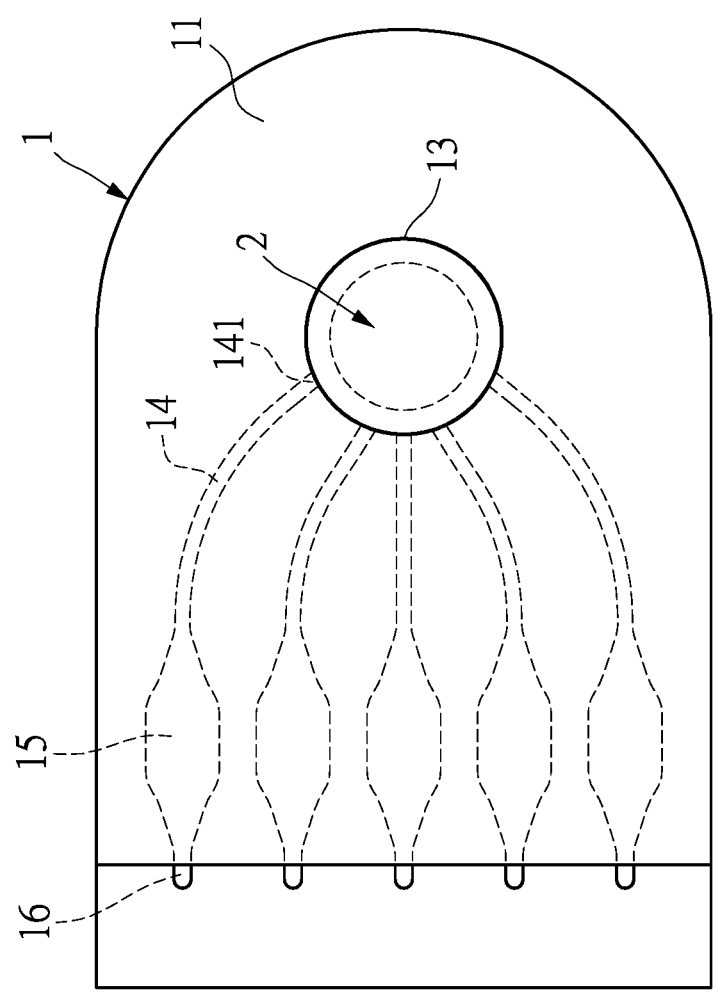
FIG. 7 is a top view of the second embodiment of the test strip device of the present disclosure.
Figure 8:
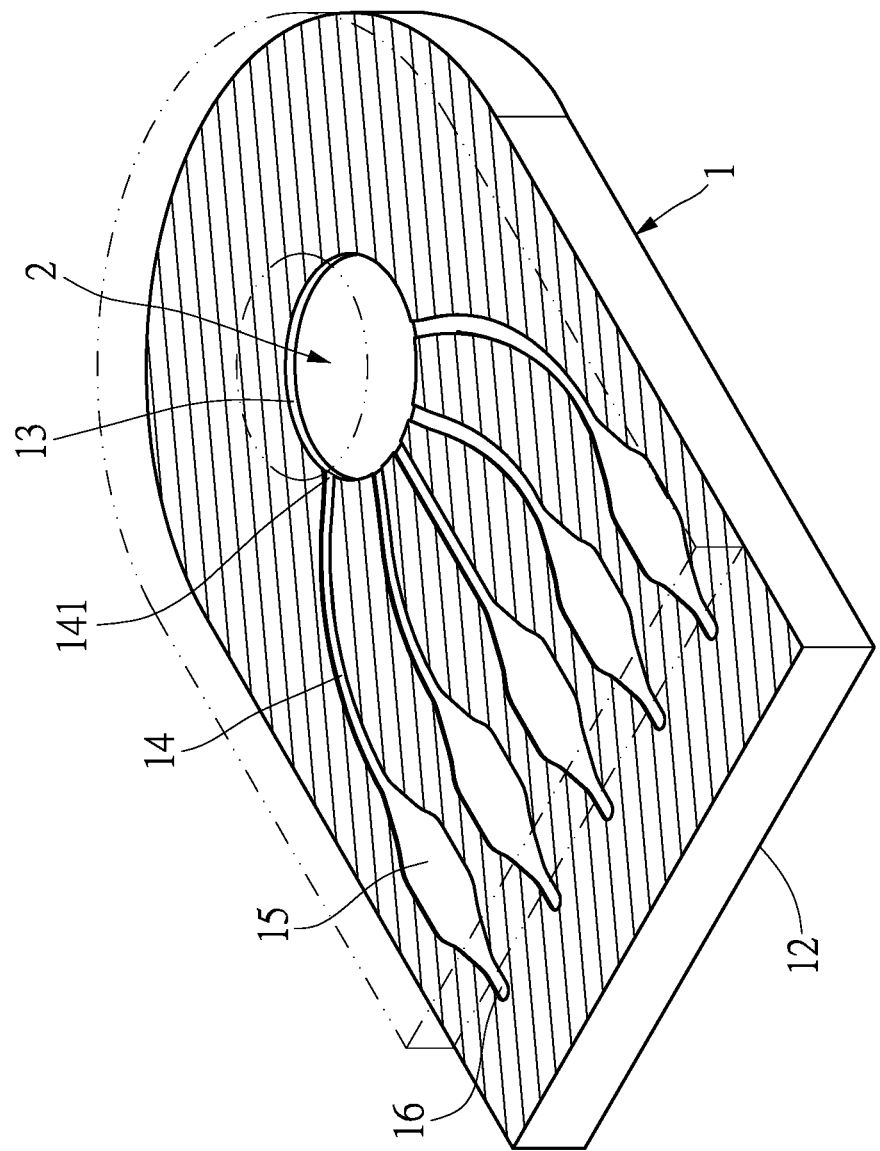
FIG. 8 is another perspective view of the second embodiment of the test strip device of the present disclosure.

Referring to FIG. 6 to FIG. 8, the present embodiment is generally the same as the first embodiment, and the major differences between them are only variation of the shape of the strip body 1, and that in the present embodiment, the injection opening 13 is arranged proximal to one side of the strip body 1, the reaction receptacles 15 are arranged proximal to the other side of the strip body 1, and the flow channels 14 are elongated and in fluid communication between the injection opening 13 and the reaction receptacles 15 respectively. An air vent 16 may be arranged at one end of each reaction receptacle 15 distal from the flow channel 14. The air vent 16 is arranged on the first face 11 and is in fluid communication with the reaction receptacle 15. In the present embodiment, the first face 11 is step-shaped and the air vent 16 is arranged on a lower portion of the first face 11.

Figure 9:
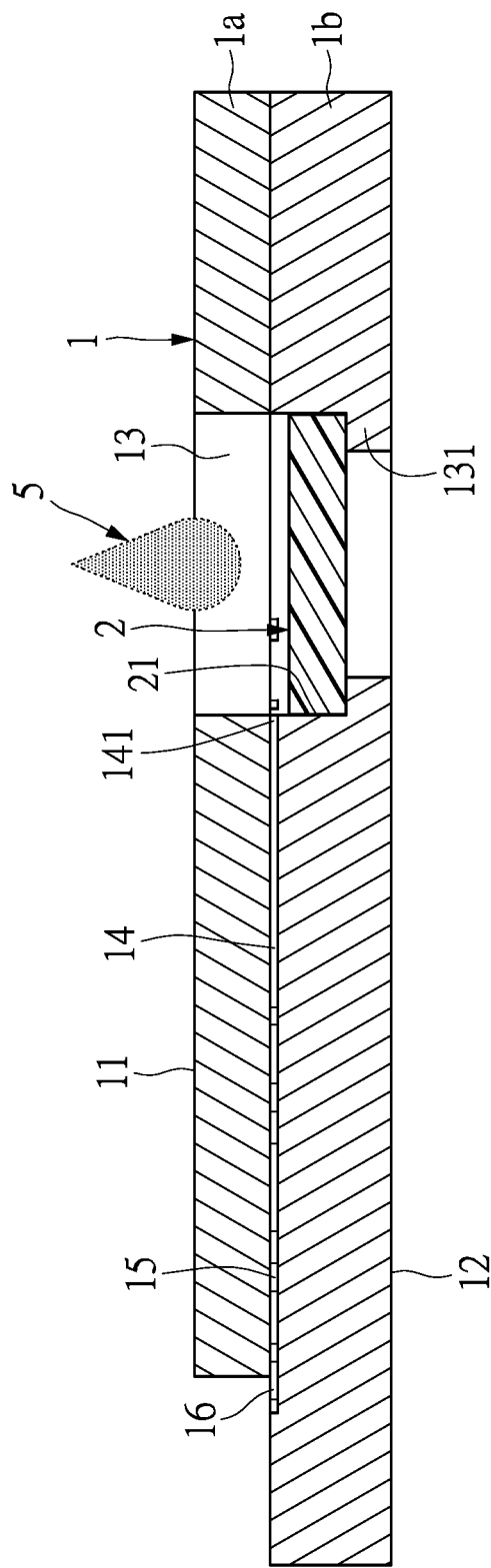
FIG. 9 is a cross-sectional view of the second embodiment of the test strip device of the present disclosure.
Figure 10:
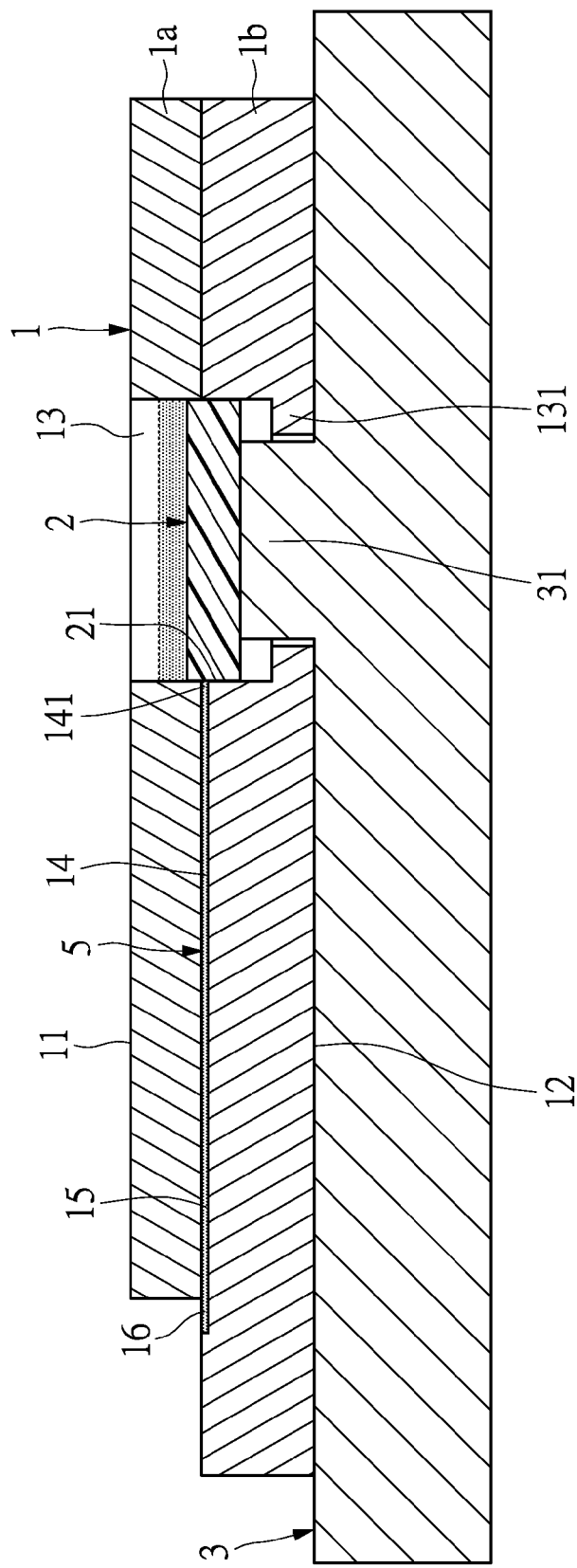
FIG. 10 is a cross-sectional view of the second embodiment of the test strip device of the present disclosure in a blocked state.

As shown in FIG. 9 and FIG. 10, after the sample 5 is injected, the reaction receptacle 15 is filled with the sample 5 by the capillary force of each flow channel 14. Then, the strip body 1 may be disposed on the tray 3, and the blocking element 2 raised to a suitable height by pressing against the blocking element 2 with the protruding portion 31, such that the blocking face 21 of the blocking element 2 closes the flow channel opening 141 to obstruct the path of back flow of the sample 5, thereby preventing possible diffusion of pollutants among the reaction receptacles 15 and back flow.

Figure 11:
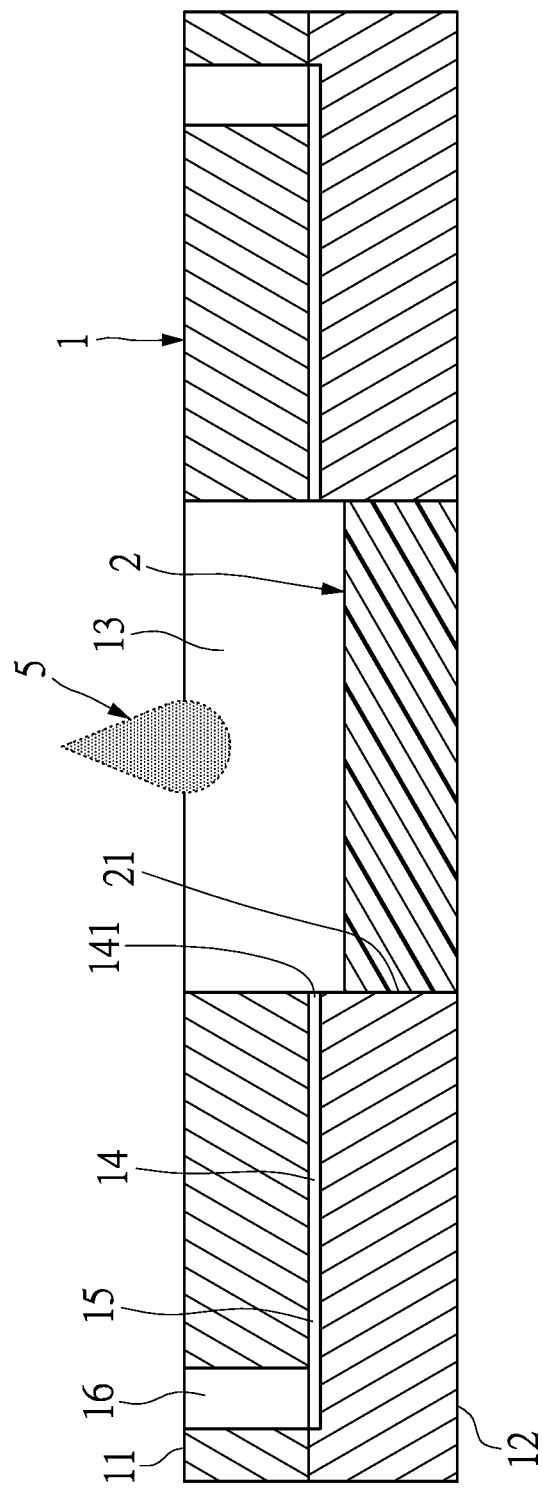
FIG. 11 is a cross-sectional view of a third embodiment of the test strip device of the present disclosure.
Figure 12:
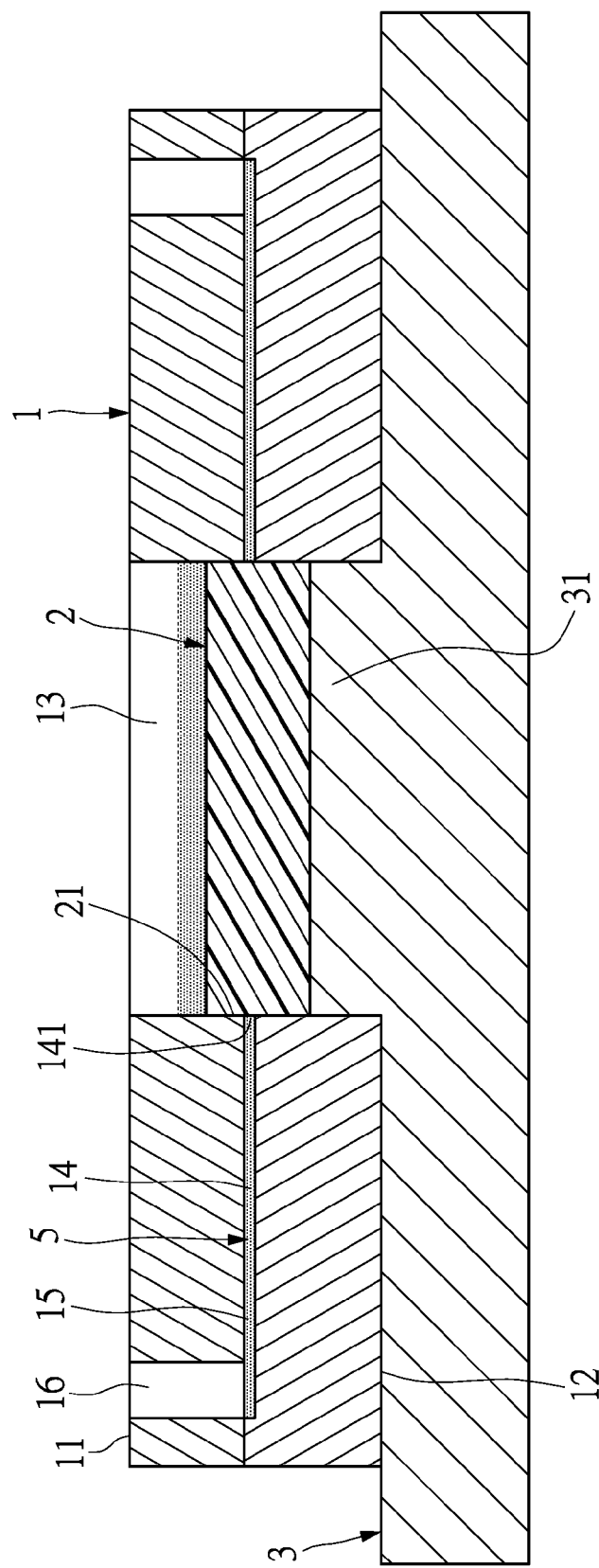
FIG. 12 is a cross-sectional view of the third embodiment of the test strip device of the present disclosure in a blocked state.

Referring to FIG. 11 and FIG. 12, the present embodiment is generally the same as the first embodiment, and the major difference between them is only the omission of the aforementioned bearing portion 131 in the present embodiment. Even without the bearing portion 131, the blocking element 2 can still maintain proper tightness with the inner wall of the injection opening 13, such that the blocking element 2 is disposed in the injection opening 13. When the strip body 1 is disposed on the tray 3, the blocking element 2 may be raised to a suitable height by pressing against the blocking element 2 with the protruding portion 31, such that the blocking face 21 of the blocking element 2 closes the flow channel opening 141 to obstruct the path of back flow of the sample 5, thereby preventing possible diffusion of pollutants among the reaction receptacles 15 and back flow.

Fourth Embodiment

Figure 13:
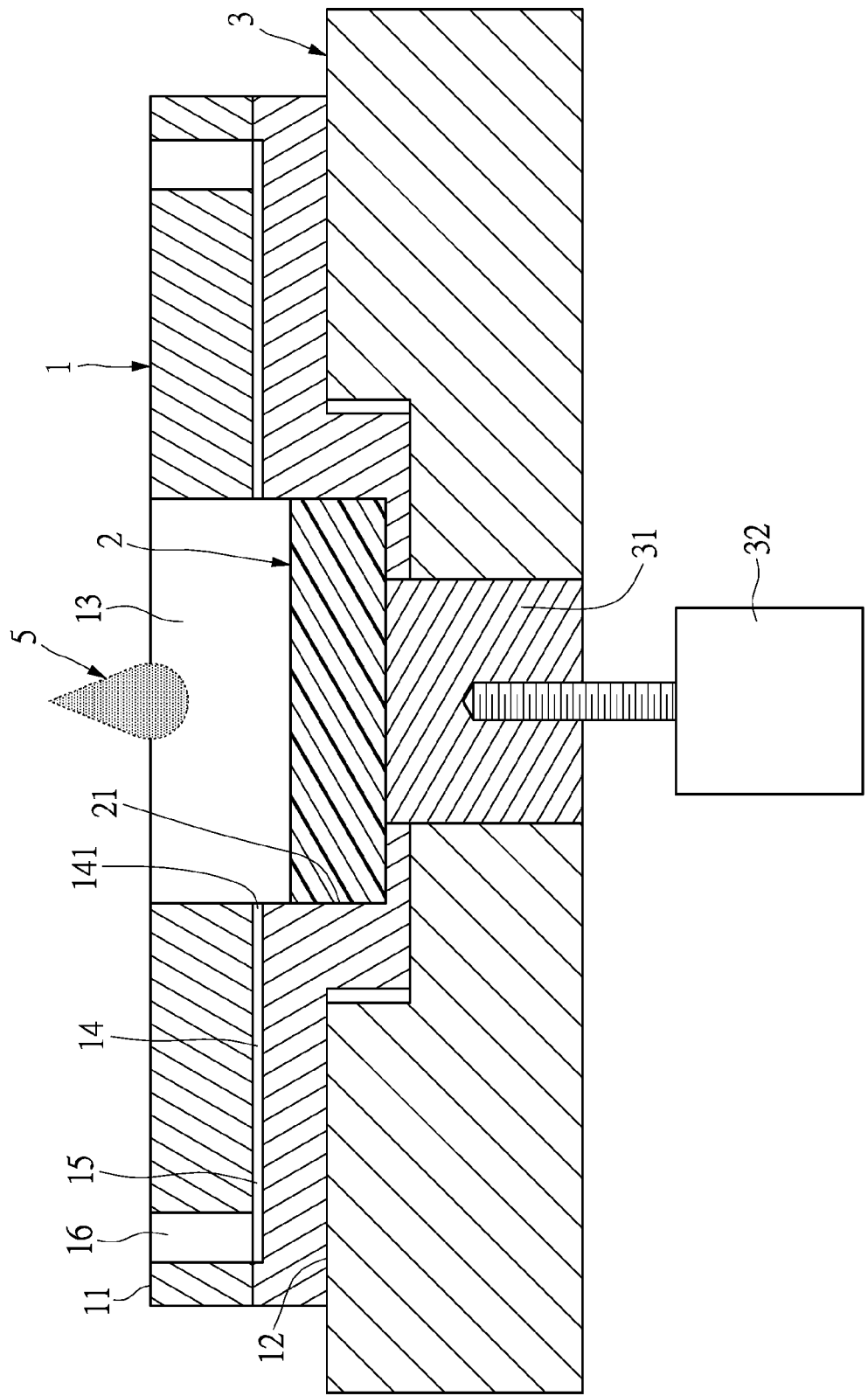
FIG. 13 is a cross-sectional view of a fourth embodiment of the test strip device of the present disclosure.
Figure 14:
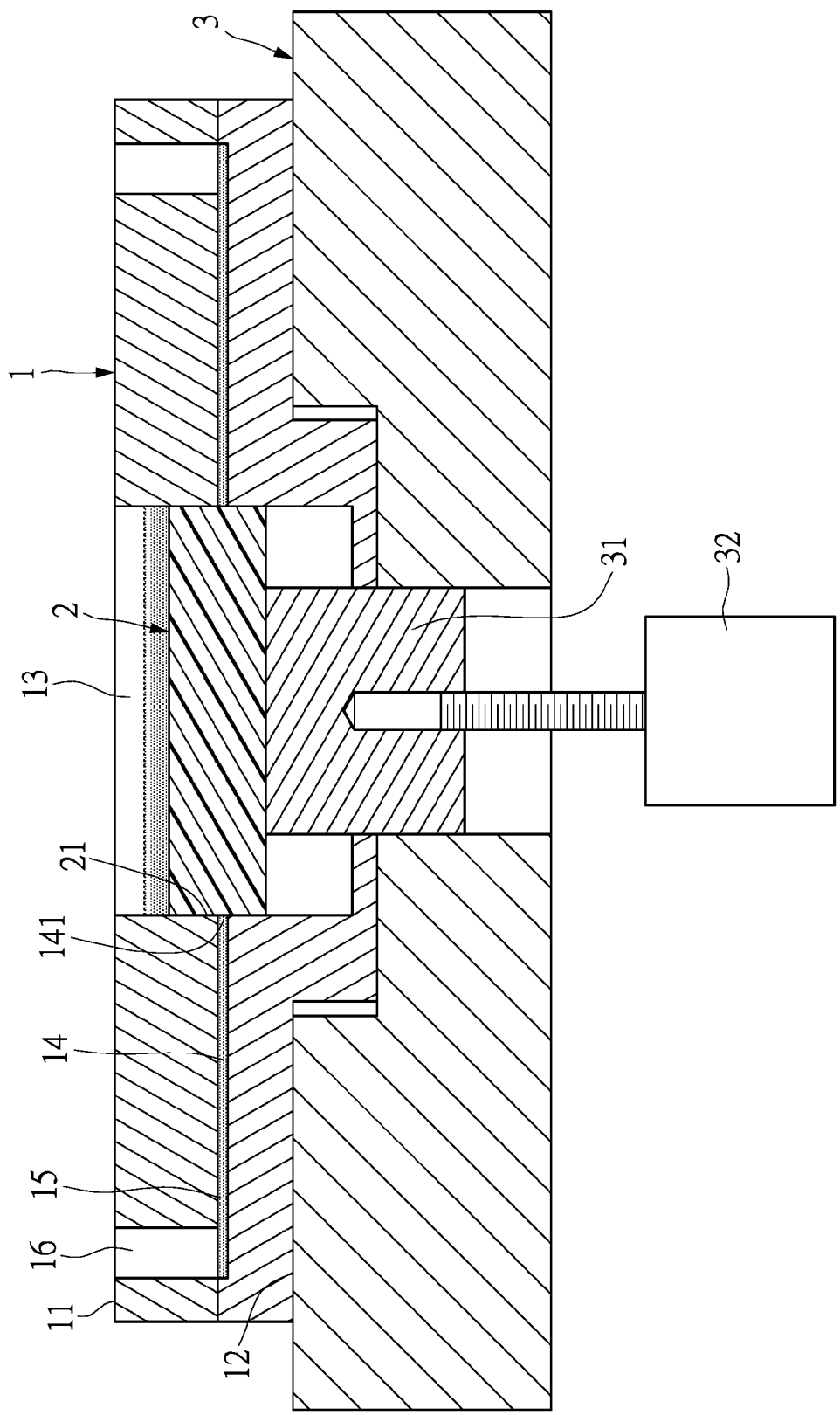
FIG. 14 is a cross-sectional view of the fourth embodiment of the test strip device of the present disclosure in a blocked state.

Referring to FIG. 13 and FIG. 14, the present embodiment is generally the same as the first embodiment, and the major difference between them is only that, the protruding portion 31 is vertically movably disposed on the tray 3; that is, the protruding portion 31 can be connected to a source of driving force 32 such as a motor for driving the protruding portion 31 vertically. When the strip body 1 is placed on the tray 3, the source of driving force 32 may be used to drive the protruding portion 31 upward to press against the blocking element 2, such that the blocking element 2 is raised to a suitable height, whereby the blocking face 21 of the blocking element 2 closes the flow channel opening 141 to obstruct the path of back flow of the sample 5, thereby preventing possible diffusion of pollutants among the reaction receptacles 15 and back flow.

The descriptions above are only preferred embodiments of the present disclosure and are not intended to limit the scope of the present disclosure. All equivalent changes made according to the specification and drawings of the present disclosure should fall within the scope of the present disclosure.

What is claimed is:

1. A test strip device, comprising:
   a strip body having a first face and a second face at opposite sides thereof and having an injection opening, a flow channel and a reaction receptacle, wherein the injection opening reaches the first face, the flow channel is in fluid communication between the injection opening and the reaction receptacle, and the flow channel is in fluid communication with the injection opening through a flow channel opening;
   a blocking element vertically movably disposed in the injection opening and selectively closing the flow channel opening, and
   a tray having a protruding portion protruding from a top face of the tray;
   wherein the protruding portion has an outer diameter smaller than an inner diameter of the injection opening, and the protruding portion is configured to be inserted into the injection opening and to upwardly press against the blocking element, such that the blocking element is raised to close the flow channel opening.

2. The test strip device according to claim 1, wherein the strip body has an air vent disposed on the first face and in fluid communication with one end of the reaction receptacle distal from the flow channel.

3. The test strip device according to claim 1, wherein the injection opening reaches the second face, an inner wall of the injection opening has a bearing portion proximal to the second face, and the blocking element is disposed on the bearing portion.

4. The test strip device according to claim 1, wherein a plurality of the flow channels and a plurality of the reaction receptacles are provided, the plurality of the flow channels are in fluid communication between the injection opening and the plurality of the reaction receptacles, respectively, and the plurality of the flow channels and the plurality of the reaction receptacles are disposed at a periphery of the injection opening, and the plurality of the flow channels and the plurality of the reaction receptacles are disposed in a radiating arrangement.

5. The test strip device according to claim 1, wherein a plurality of the flow channels and a plurality of the reaction receptacles are provided, the injection opening is arranged proximal to one side of the strip body, the plurality of the reaction receptacles are arranged proximal to the other side of the strip body, and the plurality of the flow channels are elongated and in fluid communication between the injection opening and the plurality of the reaction receptacles, respectively.

6. The test strip device according to claim 1, wherein the flow channel and the reaction receptacle are located between the first face and the second face, and disposed spaced apart from the first face and the second face.

7. The test strip device according to claim 1, wherein an outer edge of the blocking element is formed with a blocking face, and the blocking element selectively closes the flow channel opening with the blocking face.

8. The test strip device according to claim 1, wherein the injection opening is in the shape of a circular aperture, and the blocking element is a circular sheet corresponding to the injection opening.

9. The test strip device according to claim 1, wherein the blocking element is made of silica gel or rubber.

10. A test strip device, comprising:
a strip body having a first face and a second face at opposite sides thereof and having an injection opening, a flow channel and a reaction receptacle, wherein the injection opening reaches the first face, the flow channel is in fluid communication between the injection opening and the reaction receptacle, and the flow channel is in fluid communication with the injection opening through a flow channel opening;
a blocking element vertically movably disposed in the injection opening and selectively closing the flow channel opening; and
a tray having a protruding portion vertically movably disposed on the tray;
wherein the protruding portion has an outer diameter smaller than an inner diameter of the injection opening, and the protruding portion is configured to be inserted into the injection opening and to upwardly press against the blocking element, such that the blocking element is raised to close the flow channel opening.

11. The test strip device according to claim 10, wherein the strip body has an air vent disposed on the first surface and in fluid communication with one end of the reaction receptacle distal from the flow channel.

12. The test strip device according to claim 10, wherein the injection opening reaches the second face, an inner wall of the injection opening has a bearing portion proximal to the second face, and the blocking element is disposed on the bearing portion.

13. The test strip device according to claim 10, wherein a plurality of the flow channels and a plurality of the reaction receptacles are provided, the plurality of the flow channels are in fluid communication between the injection opening and the plurality of the reaction receptacles, respectively, and the plurality of the flow channels and the plurality of the reaction receptacles are disposed at a periphery of the injection opening, and the plurality of the flow channels and the plurality of the reaction receptacles are disposed in a radiating arrangement.

14. The test strip device according to claim 10, wherein a plurality of the flow channels and a plurality of the reaction receptacles are provided, the injection opening is arranged proximal to one side of the strip body, the plurality of the reaction receptacles are arranged proximal to the other side of the strip body, and the plurality of the flow channels are elongated and in fluid communication between the injection opening and the plurality of the reaction receptacles, respectively.

15. The test strip device according to claim 10, wherein the flow channel and the reaction receptacle are located between the first face and the second face, and disposed spaced apart from the first face and the second face.

16. The test strip device according to claim 10, wherein an outer edge of the blocking element is formed with a blocking face, and the blocking element selectively closes the flow channel opening with the blocking face.

17. The test strip device according to claim 10, wherein the injection opening is in the shape of a circular aperture, and the blocking element is a circular sheet corresponding to the injection opening.

18. The test strip device according to claim 10, wherein the blocking element is made of silica gel or rubber.

19. The test strip device according to claim 10, wherein the protruding portion is driven by a motor.

* * * * *